US006585980B1

United States Patent
Chan et al.

(10) Patent No.: US 6,585,980 B1
(45) Date of Patent: Jul. 1, 2003

(54) FLAGELLIN GENE, FLAC OF CAMPYLOBACTER

(75) Inventors: Voon Loong Chan, Toronto (CA); Helena Louie, Markham (CA)

(73) Assignee: The University of Toronto, Toronto (CA)

( * ) Notice: Subject to any disclaimer, the term of this patent is extended or adjusted under 35 U.S.C. 154(b) by 0 days.

(21) Appl. No.: 09/573,885

(22) Filed: May 19, 2000

Related U.S. Application Data

(63) Continuation of application No. 08/837,317, filed on Apr. 11, 1997, now Pat. No. 6,211,159.

(51) Int. Cl.$^7$ ............................................. A61K 39/02
(52) U.S. Cl. ........................... 424/234.1; 424/241.1; 424/185.1; 424/184.1; 424/197.1; 424/282.1; 424/93.1; 424/93.4; 424/826; 530/350; 435/6; 435/69.1; 514/44
(58) Field of Search .................. 530/350; 424/160, 424/234, 197.1, 185.1, 241.1, 234.1, 184.1, 282.1, 93.1, 93.4, 826; 435/6, 69.1; 514/44

(56) References Cited

U.S. PATENT DOCUMENTS

| 5,516,630 A | 5/1996 | Ticehurst et al. |
| 6,211,159 B1 * | 4/2001 | Chan et al. ........................ 514/44 |

FOREIGN PATENT DOCUMENTS

| WO | 92/13102 | 8/1992 |
| WO | 94/12641 | 6/1994 |

OTHER PUBLICATIONS

Collins, AL et al, Journal of Bacteriology, 1976, vol. 128(3), pp. 754–765 (abstract only).*

Hahnenberget, KM et al, Journal of Molecular Biology, vol. 194(1), pp. 91–103, Mar. 5, 1987, (abstract only).*

Joys, TM et al, Infection and Immunity, vol. 59(6), pp. 3330–3332, Sep. 1991, Epitope mapping of the d Flagellar antigen of Salmonella muenchen.*

Kapatral, V et al, Molecular Microbiology, vol. 17(1), pages 49–56, 1995.*

Komeda, Y et al, Molecular and general genetics, vol. 194(1–2), pp. 49–51, 1984 (abstract only).*

McGee, Karen et al, Journal of Bacteriology, vol. 178(9), pp. 5188–5198, Sep. 1996.*

Milton, DL et al, Journal of Bacteriology, vol. 178(5), pp. 1310–1319, Mar. 1996.*

Norqvist, Anders, et al, Applied and Environmental Microbiology, vol. 55(6), pp. 1400–1405, Jun. 1989.*

Stewart, BJ et al, Molecular Microbiology, Apr. 1996, vol. 20(1), pp. 137–149, (abstract only).*

Tsuda, M et al, Journal of Bacteriology, vol. 153(2), pp. 1018–1026, Feb. 1983 (abstract only).*

Chan, VL et al, EMBL abstract, accession No. U85622.1 created date Mar. 6, 1997.*

(List continued on next page.)

Primary Examiner—Lynette R. F. Smith
Assistant Examiner—Ginny Allen Portner
(74) Attorney, Agent, or Firm—Sim & McBurney

(57) ABSTRACT

Purified and isolated nucleic acid molecules are provided which encode a FlaC flagellin protein of a strain of Campylobacter, particularly *C. jejuni*, or a fragment or an analog of the FlaC flagellin protein. The nucleic acid molecules may be used to produce proteins free of contaminants derived from bacteria normally containing the FlaA or FlaB proteins for purposes of diagnostics and medical treatment. Furthermore, the nucleic acid molecules, proteins encoded thereby and antibodies raised against the proteins, may be used in the diagnosis of infection.

4 Claims, 3 Drawing Sheets

OTHER PUBLICATIONS

Figure 3:
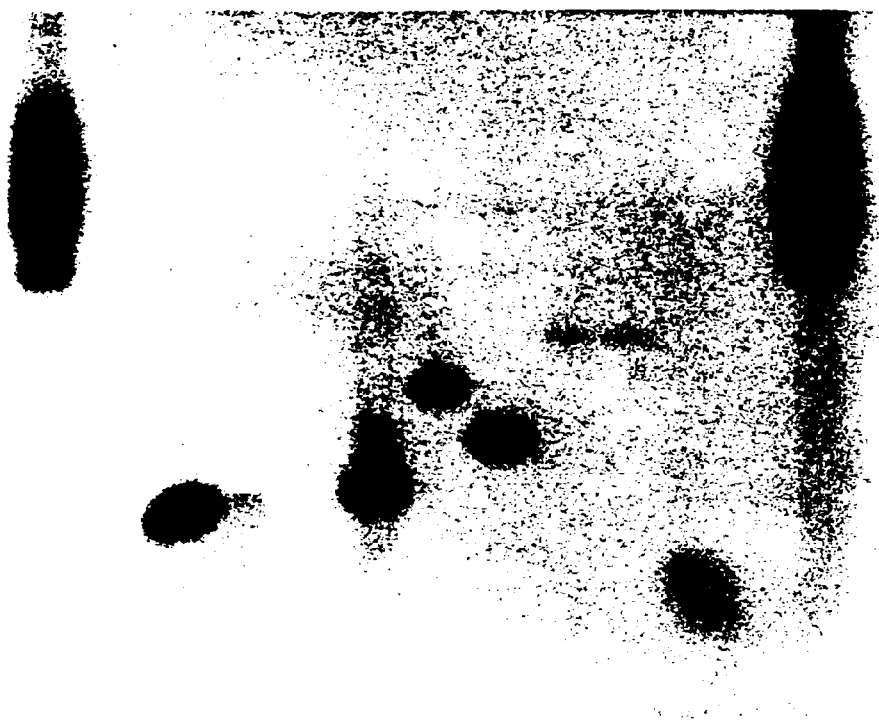

Penner J.L., (1988) Clin. Microbiol. Rev. 1: 157.
Macnab, Robert M. (1992) Annu. Rev. Genet. 26: 131–58.
Blaser, M.J. and L.B. Reller. (1981) New Engl. J. Med 305: 1444–1452.
Chan, V.L. et al., (1995) Gene 164:25–31.
Grant, C.C.R. et al., (1993) Infect. Immun. 61:1764–1771.
Guerry, P. et al., (1991) J. Bacteriol. 173:4757–4764.
Morooka, T.A. et al., (1985) J.Gen. Microbiol. 131:1973–1980.
Wassenaar, T.M. et al., (1995) Can. J. Microbiol. 141:95–101.
Yao, R. et al., (1994) Mol. Microbiol. 14:883–893.
Newell, D.G. et al., (1985) J. Hyg. 95:217–227.
Pavlovskis, O.R. et al., (1991) Infect. Immun. 59:2259–2264.
Alm, R.A. et al., (1993) J. Bacteriol. 175:3051–3057.
Driks,A.R. et al., (1989) J. Mol. Biol. 206:627–636.
Fischer, S.H. and I. Nachamkin. (1991) Mol. Microbiol. 5:1151–1158.
Josenhans C.A. et al., (1995) J. Bacteriol. 177:3010–3020.
Khawaja, R.K. et al., (1992) Curr. Microbiol. 24:213–221.
Kostrzynska, M. et al., (1991) J. Bacteriol. 173:937–946.
McCarter, L.L. (1995) J. Bacteriol. 177:1595–1609.
Minnich, S.A. et al., (1988) J. Bacteriol. 170:3953–3960.
Nuijten, P.J.M. et al., (1990) J. Biol. Chem. 265:17798–17804.
Pleier, E. and R. Schmitt. (1991) J. Bacteriol.173:2077–2085.
O'Hagan (1992) Clin Pharmokinet. 22:1.
Ulmer et al., (1993) Curr. Opinion Invest. Drugs. 2(9):983–989.
Nixon–George et al., (1990) J. Immunol. 14:4798.
Weismuller et al., (1989) Vaccine 8:29.
Deres et al., (1989) Nature 342:651.
Chang et al., (1978) Nature 275:617.
Itakura et al., (1977) Science 198:1056.
Goeddel et al., (1979) Nature 281:544.
Kim et al, J. Bacteriol. 175: 7468–7470.
Chan et al., (1996) Genbank Accession No. U85622, Abstract.
Taylor, M. F. et al., Mol. Biol. Envol., vol. 10(6), 1259–1272, Genband Accession No. L16849.
Moon, K. H. et al, J. Micro. Biotechnol., No1.6, 145–146, Genbank Accession No. U50077.
Wilson et al., Nature Vol. 368 (6466), 32–38, Genbank Accession No. U41263 or U21322.
Williams, J.G. et al., EMBO J. vol. 4(4), 999–1006, Abstract, Accession No. X02407.
Lanar et al., Science vol. 234, 593–596, Abstract, Accession No. M14163.
Laclette et al., Mol. Biochem Paras., vol. 44, 287–296, Abstract, Accession No. M35499.

* cited by examiner

| | | |
|---|---|---|
| 1 | ATTTGTTTTTATTTTACTAATACCATAATTGAACTCCAAAACTTAGGCGAAAACACTACAAAAACTCAAGAATTTATCAGCATCCATAA | 90 |
| 91 | TGCAAGTGAAGTGGTGATTAAAATCATCTTGATAATGCAAGTTTTTTTATATTTCTTAAGCTTTAAAATAGCAAAAAAATGATAAAATAT | 180 |
| 181 | TAAATAAATCCAAAAGAGAAGGAGTAGGCCATGATGATCTCTGATGCAACTATGATGCAACAAAATTATTATTTAAATAATGCACAAAAA | 270 |
| |                                       M  M  I  S  D  A  T  M  M  Q  Q  N  Y  Y  L  N  N  A  Q  K | 20 |
| 271 | GCTAGCGATAAAGCTTTAGAAAATATTGCAGCTGTTCGCGCAATAAGTGGAGTTGATAGTGCTAATTTAGCTATTGCTGATTCTTTAAGA | 360 |
| 21 | A  S  D  K  A  L  E  N  I  A  A  V  R  A  I  S  G  V  D  S  A  N  L  A  I  A  D  S  L  R | 50 |
| 361 | TCTCAATCAAGCACTATAGATCAAGGTGTCGCAAATGCTTATGATGCTATAGGGGTTTTACAAATTGCAGATGCTAGCCTTACCAATATC | 450 |
| 51 | S  Q  S  S  T  I  D  Q  G  V  A  N  A  Y  D  A  I  G  V  L  Q  I  A  D  A  S  L  T  N  I | 81 |
| 451 | TCTCAAAGCGCAGATAGACTTAATGAACTTTCAGTAAAAATGAACAATGCTGCACTTAATGATTCTCAAAAAGGAATGCTAAGAACAGAA | 540 |
| 81 | S  Q  S  A  D  R  L  N  E  L  S  V  K  M  N  N  A  A  L  N  D  S  Q  K  G  M  L  R  T  E | 110 |
| 541 | GCAACACGCATACAAGAATCCATCAATGATTCTTTTAATAATGCAACTTATAATGGAAAAAATGTCTTTCAAACTATGAATTTTGTAGTA | 630 |
| 111 | A  T  R  I  Q  E  S  I  N  D  S  F  N  N  A  T  Y  N  G  K  N  V  F  Q  T  M  N  F  V  V | 140 |
| 631 | GGTAGCGGAACTGAAACTACAAATTTAAATCCATTAGCAACAGATGGATTAAGCATAGATAATCAAGATAGTATTACAAATTTTATGGAT | 720 |
| 141 | G  S  G  T  E  T  T  N  L  N  P  L  A  T  D  G  L  S  I  D  N  Q  D  S  I  T  N  F  M  D | 170 |
| 1 | CAACTTGGAAGTTTAAGAAGTGAAATAGGCTCAGGTATCAATGCCATCACATCAAATATTAATGCAAGTGTTCAAAATAGCATCAACTCA | 810 |
| 1 | Q  L  G  S  L  R  S  E  I  G  S  G  I  N  A  I  T  S  N  I  N  A  S  V  Q  N  S  I  N  S | 200 |
| 811 | AAAGCAGCTGAAAATAATTTACTAAATAATGACATGGCAAAAAATGTCAATGATTTTAATGCCAATTATCTAAAAGAAAATGCTGCTGCT | 900 |
| 201 | K  A  A  E  N  N  L  L  N  N  D  M  A  K  N  V  N  D  F  N  A  N  Y  L  K  E  N  A  A  A | 230 |
| 901 | TTTGTTGCTGCGCAATCCAACATGCAGCTTCAAAGCAAAATTGCTAATTTATTACAATAAAATAAGCCCTAAATAGGGCTTATTTTTAT | 990 |
| 231 | F  V  A  A  Q  S  N  M  Q  L  Q  S  K  I  A  N  L  L  Q | 249 |
| 991 | CAAAATGACTTTAGAGCAAATTTTAGAAAAAACCAAAAACGTTCGTCTTGTAGCGGCAAGCAAGTATGTCGATGCAAGTATAATTGAAAA | 1080 |
| 1081 | GCTTTTTGATCAAGGTATAGTAGAA | |

FIG. 1

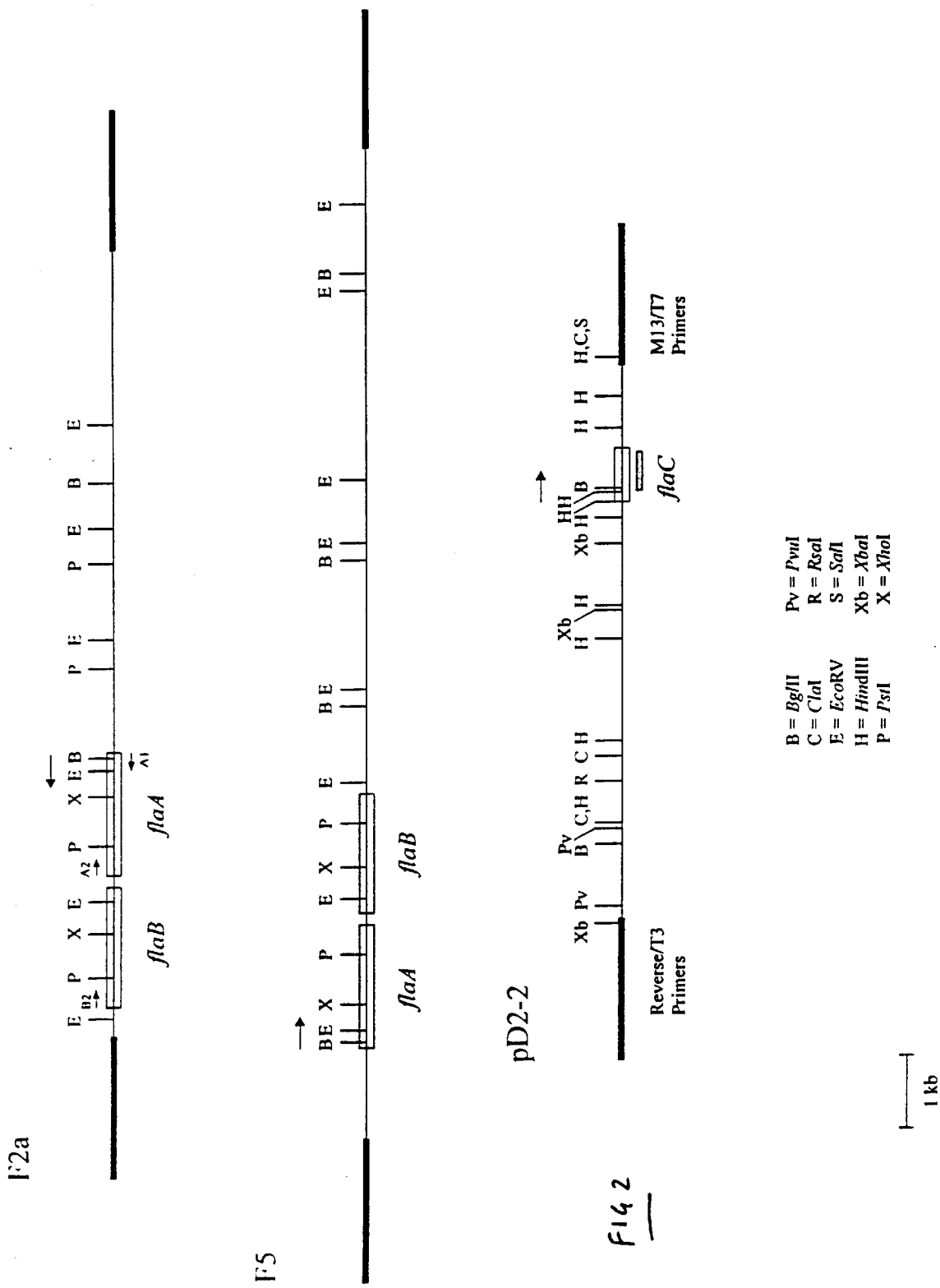

FLAGELLIN GENE, FLAC OF CAMPYLOBACTER

REFERENCE TO RELATED APPLICATION

This application is a continuation of U.S. patent application Ser. No. 08/837,317 filed Apr. 11, 1997 (now U.S. Pat. No. 6,211,159).

FIELD OF THE INVENTION

The present invention is related to the molecular cloning of a gene encoding a flagellin protein, identified herein as FlaC, of the flagellar filament from a strain of Campylobacter.

BACKGROUND OF THE INVENTION

*Campylobacter jejuni* is a Gram-negative spiral microaerophilic bacterium that has been recognized as a cause of secretory type diarrhea and enteritis. (Ref. 1). Throughout this application, various references are referred to in parenthesis to more fully describe the state of the art to which this invention pertains. Full bibliographic information for each citation is found at the disclosed end of the specification immediately preceding the claims. These references are hereby incorporated by reference into the present disclosure). The flagellum of *C. jejuni* is responsible for bacterial motility which enhances the organism's pathogenicity. The flagellum consists of three major components; the filament, the hook, and the basal body (Ref. 2). A campylobacter cell carries a single unsheathed flagellum at one or both poles of the body. The flagella are responsible for the high motility of the organisms as aflagellate mutants are nonmotile (Refs. 3, 4, 5, 6, 7, 8, 9). A number of studies indicated that the polar flagellum plays an important role in colonization of the viscous mucus lining of the gastric intestinal tract and that it is an important virulence determinant (Refs. 3,4,7,10,11).

The basic structure of the bacterial flagellum consists of a propeller (filament) connected via a universal joint (hook) to a transmission shaft, motor and brushings (basal body) embedded in the cell envelope (Ref. 12). The flagellar filament consists of several thousand self-assembling protein (flagellin) monomers arranged in a helix. These form a hollow tube of relatively constant diameter and variable length with an over corkscrew morphology.

Most eubacterial flagellar filaments that have been characterized appear to be composed of a single kind of flagellin (Ref. 8). However a number of Eubacteria have now been shown to possess multiple flagellin genes (Refs. 6, 13, 14, 15, 16, 17, 18, 19, 20, 21, 22), *C jejuni* (Refs. 13, 15, 17, 21) and *C. coli* (Refs. 6, 13) have been reported to have two flagellin genes (flaA and flaB). In *C. jejuni,* the flagellin genes flaA and flaB have been isolated and sequenced, however prior to the present invention a third flagellin gene had not been isolated and characterized.

It would be advantageous to provide nucleic acid molecules encoding flagellin proteins of the flagella for strains of Campylobacter and purified flagellin proteins, including flaC for use as antigens, immunogenic compositions, including vaccines, carriers for other antigens and immunogens and the generation of diagnostic reagents.

SUMMARY OF THE INVENTION

The present invention is directed towards the provision of purified and isolated nucleic acid molecules encoding a flagellin protein C (FlaC) of a strain of Campylobacter or a fragment or an analog of the flagellin protein. The nucleic acid molecules provided herein are useful for the specific detection of strains of Campylobacter, and for diagnosis of infection by Campylobacter. The purified and isolated nucleic acid molecules provided herein, such as DNA, are also useful for expressing the flac gene by recombinant DNA means for providing, in an economical manner, purified and isolated FlaC proteins, subunits, fragments or analogs thereof. The FlaC protein, subunits or fragments thereof or analogs thereof, as well as nucleic acid molecules encoding the same and vectors containing such nucleic acid molecules, are useful in immunogenic compositions against diseases caused by Campylobacter, the diagnosis of infection by Campylobacter and as tools for the generation of immunological reagents. Monoclonal antibodies or monospecific antisera (antibodies) raised against the FlaC protein produced in accordance with aspects of the present invention are useful for the diagnosis of infection by Campylobacter, the specific detection of Campylobacter (in for example in vitro and in vivo assays) and for the treatment of diseases caused by Campylobacter.

Peptides corresponding to portions of the FlaC protein or analogs thereof are useful immunogenic compositions against disease caused by Campylobacter, the diagnosis of infection by Campylobacter and as tools for the generation of immunological reagents. Monoclonal antibodies or antisera raised against these peptides, produced in accordance with aspects of the present invention, are useful for the diagnosis of infection by Campylobacter, the specific detection of Campylobacter (in, for example, in vitro and in vivo assays) and for use in passive immunization as a treatment of disease caused by Campylobacter.

In accordance with one aspect of the present invention, there is provided a purified and isolated nucleic acid molecule encoding a flagellin protein (FlaC) of flagellum of a strain of Campylobacter, more particularly, a strain of *Campylobacter jejunis,* or a fragment or an analog of the FlaC protein.

In one preferred embodiment of the invention, the nucleic acid molecule may encode the FlaC protein of the Campylobacter strain.

In another aspect of the present invention, there is provided a purified and isolated nucleic acid molecule having a nucleotide sequence selected from the group consisting of: (a) the entire nucleotide sequence set out in FIG. 1 (SEQ ID No: 1), or the complementary sequence of said sequence; (b) the coding nucleotide sequence set out in FIG. 1 (SEQ ID No: 2), or the complementary sequence of said sequence; (c) a nucleotide sequence encoding the amino acid sequence set forth in FIG. 1 (SEQ ID No: 3); and (d) a nucleotide sequence which hybridizes under stringent conditions to any one of the sequences defined in (a), (b) or (c). The DNA sequence defined in (c) preferably has at least about 90% sequence identity with any one of the DNA sequences defined in (a) and (b).

In an additional aspect, the present invention includes a vector adapted for transformation of a host, comprising a nucleic acid molecule as provided herein. The vector may be one having the characteristics of plasmid pD2-2.

The plasmids may be adapted for expression of the encoded FlaC protein, fragments or analogs thereof, in a heterologous or homologous host, in either a lipidated or non-lipidated form. Accordingly, a further aspect of the present invention provides an expression vector adapted for transformation of a host comprising a nucleic acid molecule as provided herein and expression means operatively coupled to the nucleic acid molecule for expression by the host of the FlaC protein or the fragment or analog of the FlaC protein. In specific embodiments of this aspect of the invention, the nucleic acid molecule may encode substantially all the FlaC protein of the Campylobacter strain. The expression means may include a nucleic acid portion encoding a leader sequence for secretion from the host of the FlaC protein or the fragment or the analog of the FlaC protein. The expression means also may include a nucleic acid portion encoding a lipidation signal for expression from the host of a lipidated form of the FlaC protein or the fragment or the analog of the FlaC protein. The host may be selected from, for example, *Escherichia coli,* Bordetella, Bacillus, Haemophilus, Moraxella, fungi, yeast or baculovirus and Semliki Forest virus expression systems may be used.

In an additional aspect of the invention, there is provided a transformed host containing an expression vector as provided herein. The invention further includes a recombinant FlaC protein or fragment or analog thereof producible by the transformed host. Further aspects of the present invention provide an isolated and purified FlaC protein of a Campylobacter strain substantially free from other proteins of the Campylobacter strain. The Campylobacter strain may be *C. jejuni*.

The present invention further provides synthetic peptides corresponding to portions of the FlaC protein. Accordingly, in a further aspect of the invention, there is provided a synthetic peptide having no less than six amino acids and no more than 150 amino acids and containing an amino acid sequence corresponding to a portion only of a FlaC protein of a strain of Campylobacter or of a fragment or an analog of the FlaC protein.

In accordance with another aspect of the invention, an immunogenic composition is provided which comprises at least one active component selected from at least one nucleic acid molecule as provided herein, at least one recombinant protein as provided herein, at least one of the purified and isolated FlaC protein, as provided herein and at least one synthetic peptide as provided herein, and a pharmaceutically acceptable carrier therefor or vector therefor. The at least one active component produces an immune response when administered to a host.

The immunogenic compositions provided herein may be formulated as a vaccine for in vivo administration to protect against diseases caused by bacterial pathogens that produce flagellin proteins. For such purpose, the compositions may be formulated as a microparticle, capsule, ISCOM or liposome preparation. Alternatively, the compositions may be provided in combination with a targeting molecule for delivery to specific cells of the immune system or to mucosal surfaces. The immunogenic composition may comprise a plurality of active components to provide protection against disease caused by a plurality of species of flagellin protein producing bacteria.

The immunogenic compositions of the invention (including vaccines) may further comprise at least one other immunogenic or immunostimulating material and the immunostimulating material may be at least one adjuvant or at least one cytokine. Suitable adjuvants for use in the present invention include (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide polyphosphazene, ISCOPREP, DC-chol, DDBA and a lipoprotein. Advantageous combinations of adjuvants are described in copending U.S. patent applications Ser. No. 08/261,194 filed Jun. 16, 1994 and Ser. No. 08/483,856, filed Jun. 7, 1995, assigned to the assignee hereof and the disclosures of which are incorporated herein by reference thereto.

In accordance with another aspect of the invention, there is provided a method for inducing protection against infection or disease caused by Campylobacter or other bacteria that produce flagellin protein, comprising the step of administering to a susceptible host, which may be a primate, such as a human, an effective amount of the immunogenic composition as recited above.

In accordance with another aspect of the invention, an antiserum or antibody specific for the recombinant protein, the isolated and purified FlaC protein, synthetic peptide or the immunogenic composition, is provided.

In a further aspect, there is provided a live vector for delivery of FlaC protein to a host, comprising a vector containing the nucleic acid molecule as described above. The vector may be selected from Salmonella, BCG, adenovirus, poxvirus, vaccinia and poliovirus. The nucleic acid molecule may encode a fragment of the FlaC protein of a Campylobacter strain which is conserved among bacteria that produce the FlaC protein. Such vector may be included in an immunogenic composition provided herein.

The present invention further includes a method of determining the presence of nucleic acid encoding the FlaC protein of a strain of Campylobacter, in a sample, comprising the steps of: (a) contacting the sample with the nucleic acid molecule provided herein to produce duplexes comprising the nucleic acid molecule and any said nucleic acid molecule encoding the FlaC protein of Campylobacter present in the sample and specifically hybridizable therewith; and (b) determining production of the duplexes.

In an additional aspect, the present invention provides a method of determining the presence of a FlaC protein of a Campylobacter strain in a sample, comprising the steps of (a) immunizing a subject with the immunogenic composition provided herein to produce antibodies specific for the FlaC protein; (b) contacting the sample with the antibodies to produce complexes comprising FlaC protein of a Campylobacter strain present in the sample and the FlaC protein specific antibodies; and determining production of the complexes.

A further aspect of the present invention provides a diagnostic kit for determining the presence of nucleic acid encoding the FlaC protein of a strain of Campylobacter, in a sample, comprising (a) the nucleic acid molecule provided herein; (b) means for contacting the nucleic acid with the sample to produce duplexes comprising the nucleic acid molecule and any said nucleic acid present in the sample and hybridizable with the nucleic acid molecule; and (c) means for determining production of the duplexes.

In another aspect of the present invention, there is provided a diagnostic kit for detecting the presence of a FlaC protein of a Campylobacter strain in a sample, comprising (a) a FlaC protein specific antibody to the immunogenic composition provided herein; (b) means for contacting the antibody with the sample to produce a complex comprising said FlaC protein and the antibody; and (c) means for determining production of the complex.

The invention further includes the use of the nucleic acid molecules and proteins provided herein as medicines. The invention additionally includes the use of the nucleic acid molecules and proteins provided herein in the manufacture of medicaments for protection against infection by strains of Campylobacter.

The purified and isolated DNA molecules comprising at least a portion coding for a FlaC protein of a species of Campylobacter typified by the embodiments described herein are advantageous as:

nucleic acid probes for the specific identification of Campylobacter strains in vitro or in vivo.
- the products encoded by the DNA molecules are useful as diagnostic reagents, antigens for the production of Campylobacter-specific antisera, for vaccination against the diseases caused by species of Campylobacter and (for example) detecting infection by Campylobacter.
- peptides corresponding to portions of the FlaC protein as typified by the embodiments described herein are advantageous as diagnostic reagents, antigens for the production of Campylobacter-specific antisera, for vaccination against the diseases caused by species of Campylobacter and (for example) for detecting infection by Campylobacter.

BRIEF DESCRIPTION OF DRAWINGS

The present invention will be further understood from the following description with reference to the drawings in which:

FIG. 1 shows the nucleotide sequence of flaC gene and flanking regions (SEQ ID No: 1). The translated amino acid (SEQ ID No: 3) is located below the encoding sequence (SEQ ID No: 2). The ribosome binding site (RBS), the −10 and −35 regions are indicated by lines above the sequence. The putative transcriptional start sites are indicated by an asterisk below the sequence. Inverted repeats are shown with an arrow below the sequence.

FIG. 2 contains the restriction map of clone pD2-2 in pBluescript vector. The location of the flaC is denoted by the boxed area below the restriction map. The restriction sites are : B, BglII; C, ClaI; H, HindIII; P, PvuI; R, RsaI; S,SalI; and X, XbaI. The shaded box represents vector sequences. The direction of transcription is indicated by the arrow.

FIG. 3 shows Southern Blot hybridization with flaC to HindIII digested genomic DNA from various Campylobacter species using 30% formamide. Lane 1, 100 bp molecular marker; lane 2, blank; lane 3, *C. jejuni* ATCC 43431; lane 4, *C. jejuni* OH4382; lane 5, blank; lane 6, *C. jejuni* ATCC 43446; lane 7, *C. jejuni* ATCC 33559; lane 8, *C. coli* ATCC 43474; lane 9, *C. lari* ATCC 35221; lane 10, *C. lari* PC637; Lane 11, *C. upsaliensis* ATCC 43954; lane 12, blank; lane 13, 100 bp molecular marker.

GENERAL DESCRIPTION OF THE INVENTION

Any Campylobacter strain may be conveniently used to provide the purified and isolated nucleic acid, provided herein which may be in the form of DNA molecules, comprising at least a portion of the nucleic acid coding for FlaC protein of a flagellum as typified by embodiments of the present invention. Such strains are generally available from clinical sources and from bacterial culture collections, such as the American Type Culture Collection, Rockville, Md., U.S.A. One particular useful species is *C. jejuni.*

In this application, the term "a flagellin protein C" is used to define a family of FlaC proteins which includes those having variations in their amino acid sequences including those naturally occurring in various strains of Campylobacter. The purified and isolated DNA molecules comprising at least a portion coding for the FlaC protein of the present invention also include those encoding fragments or functional analogs of the FlaC protein. In this application, a first protein is a "functional analog" of a second protein if the first protein is immunologically related to and/or has the same function as the second protein. The functional analog may be, for example, a fragment of the protein or a substitution, addition or deletion mutant thereof.

Oligonucleotide probes derived from the Fur-box sequences from the recently cloned *C. jejuni* fur gene (Ref. 4) were used to screen a pBluescript genomic library of *C. jejuni.* One of the clones sequenced, pD2-2 had an open reading frame (ORF) that codes for a polypeptide of 249 amino acid residues. This protein had the highest homology with the N-terminal region of the *C. coli* FlaA protein sequence. The open reading frame was designated FlaC as the third flagellin gene in Campylobacter.

It is clearly apparent to one skilled in the art, that the various embodiments of the present invention have many applications in the fields of vaccination, diagnosis, treatment of, for example, Campylobacter infections, and infections with other bacterial pathogens that produce FlaC protein and the generation of immunological reagents. A further non-limiting discussion of such uses is further presented below.

1. Vaccine Preparation and Use

Immunogenic compositions, suitable to be used as vaccines, may be prepared from FlaC proteins, analogs and fragments thereof, peptides and nucleic acid molecules encoding such FlaC proteins, fragments and analogs thereof and peptides as disclosed herein. The vaccine elicits an immune response which produces antibodies, including anti-FlaC protein antibodies and antibodies that are opsonizing or bactericidal. Should the vaccinated subject be challenged by Campylobacter or other bacteria that produce a FlaC protein, the antibodies bind to the basal body rod protein and thereby inactivate the bacteria. Opsonizing or bactericidal antibodies may be particularly useful for providing protection.

Vaccines containing peptides are generally well known in the art, as exemplified by U.S. Pat. Nos. 4,601,903; 4,599,231; 4,599,230; and 4,596,792; all of which references are incorporated herein by reference. Immunogenic compositions including vaccines may be prepared as injectables, as liquid solutions or emulsions. The nucleic acid molecules, FlaC protein, analogs and fragments thereof and/or peptides may be mixed with pharmaceutically acceptable excipients which are compatible with the FlaC protein, fragments analogs or peptides. Such excipients may include, water, saline, dextrose, glycerol, ethanol, and combinations thereof. The immunogenic compositions and vaccines may further contain auxiliary substances such as wetting or emulsifying agents, pH buffering agents, or adjuvants to enhance the effectiveness of the vaccines. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. The immunogenic composition may be provided in combination with a targeting molecule for delivery to specific cells of the immune system or to mucosal surfaces. Some such targeting molecules include vitamin B12 and fragments of bacterial toxins, as described in WO 92/17167 (Biotech Australia Pty. Ltd.), and monoclonal antibodies, as described in U.S. Pat. No. 5,194,254 (Barber et al). Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions take the form of solutions, suspensions, tablets, pills, capsules, sustained release formulations or powders and contain 1 to 95% of the nucleic acid molecule, FlaC protein, fragment analogs and/or peptides.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the FlaC protein, analogs and fragments thereof and/or peptides. Suitable regimes for initial administration and booster doses are also variable, but may include an initial administration followed by subsequent administrations. The dosage of the vaccine may also depend on the route of administration and will vary according to the size of the host.

Thus, the nucleic acid molecules encoding the FlaC protein, fragments or analogs thereof, of the present invention may also be used directly for immunization by administration of the nucleic acid molecule (including DNA molecules) directly, for example by injection for genetic immunization or by constructing a live vector such as Salmonella, BCG, adenovirus, poxvirus, vaccinia or poliovirus. A discussion of some live vectors that have been used to carry heterologous antigens to the immune system are discussed in, for example, O'Hagan (Ref. 23). Processes for the direct injection of DNA into test subjects for genetic immunization are described in, for example, Ulmer et al. (Ref. 24).

The use of peptides in vivo may first require their chemical modification since the peptides themselves may not have a sufficiently long serum and/or tissue half-life and/or sufficient immunogenicity. Such chemically modified peptides are referred to herein as "peptide analogs". The term "peptide analog" extends to any functional chemical equivalent of a peptide characterized by its increased stability and/or efficacy and immunogenicity in vivo or in vitro in respect of the practice of the invention. The term "peptide analog" is also used herein to extend to any amino acid derivative of the peptides as described herein. Peptide analogs contemplated herein are produced by procedures that include, but are not limited to, modifications to side chains, incorporation of unnatural amino acids and/or their derivatives during peptide synthesis and the use of cross-linkers and other methods which impose conformational constraint on the peptides or their analogs.

Examples of side chain modifications contemplated by the present invention include modification of amino groups such as by reductive alkylation by reaction with an aldehyde followed by reduction with NaBH$_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxal-5'-phosphate followed by reduction with NaBH$_4$.

The guanidino group of arginine residues may be modified by the formation of heterocyclic condensation products with reagents such as 2,3-butanedione, phenylglyoxal and glyoxal.

The carboxyl group may be modified by carbodimide activation via o-acylisourea formation followed by subsequent derivatisation, for example, to a corresponding amide.

Sulfhydryl groups may be modified by methods such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH.

Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid-, t-butylglycine, norvaline, phenylglycine, ornithine, sarcosine, 4-amino-3-hydroxy-6-methylheptanoic acid, 2-thienyl alanine and/or D-isomers of amino acids.

Immunogenicity can be significantly improved if the antigens are co-administered with adjuvants, commonly used as an 0.05 to 1.0 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminim phosphate (collectively commonly referred to as alum) are routinely used as adjuvants in human and veterinary vaccines. The efficacy of alum in increasing antibody responses to diptheria and tetanus toxoids is will established and a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes ISCOMs), pluronic polymers with mineral oil, killed mycobacteria and mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. 1991 reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. (Ref. 25), reported that octadecyl esters of aromatic amino acids complexed with a recombinant hepatitis B surface antigen, enhanced the host immune responses against hepatitis B virus.

Lipidation of synthetic peptides has also been used to increase their immunogenicity. Thus, Weismuller (Ref. 26), describes a peptide with a sequence homologous to a foot-and-mouth disease viral protein coupled to an adjuvant tripalmityl-s-glyceryl-cysteinylserylserine, being a synthetic analogue of the N-terminal part of the lipoprotein from Gram negative bacteria. Furthermore, Deres et al. (Ref. 27), reported in vivo priming of virus-specific cytotoxic T lymphocytes with synthetic lipopeptide vaccine which comprised of modified synthetic peptides derived from influenza virus nucleoprotein by linkage to a lipopeptide, N-palmityl-s-[2,3-bis(palmitylxy)-(2RS)-propyl-[R]-cysteine (TPC).

2. Immunoassays

The FlaC protein, analogs and fragments thereof and/or peptides of the present invention are useful as immunogens, as antigens in immunoassays including enzyme-linked immunosorbent assays (ELISA), RIAs and other non-enzyme linked antibody binding assays or procedures known in the art for the detection of anti-bacterial, Campylobacter, FlaC protein and/or peptide antibodies. In ELISA assays, the FlaC proteins, analogs, fragments and/or peptides corresponding to portions of FlaC protein are immobilized onto a selected surface, for example a surface capable of binding proteins or peptides such as the wells of a polystyrene microtiter plate. After washing to remove incompletely adsorbed FlaC protein, analogs, fragments and/or peptides, a nonspecific protein such as a solution of bovine serum albumin (BSA) or casein that is known to be antigenically neutral with regard to the test sample may be bound to the selected surface. This allows for blocking of nonspecific adsorption sites on the immobilizing surface and thus reduces the background caused by nonspecific bindings of antisera onto the surface. The selected peptides may be from the conserved regions of FlaC protein to enhance the cross-species detection unless one particular bacterial species is to be detected. In that event, a polypeptide is selected which is unique to the FlaC protein of that particular species. Normally, the peptides are in the range of 12 residues and up and preferably 14 to 30 residues. It is understood however, that a mixture of peptides may be used either as an immunogen in a vaccine or as a diagnostic agent. There may be circumstances where a mixture of peptides from the conserved regions and/or from the non-conserved regions are used to provide cross-species protection and/or specific diagnosis. In this instance, the mixture of peptide immunogens is commonly referred to as a "cocktail" preparation for use as a vaccine or diagnostic agent.

The immobilizing surface is then contacted with a sample such as clinical or biological materials to be tested in a manner conducive to immune complex (antigen/antibody) formation. This may include diluting the sample with diluents such as BSA, bovine gamma globulin (BGG) and/or phosphate buffered saline (PBS)/Tween. The sample is then allowed to incubate for from 2 to 4 hours, at temperatures such as of the order of 25° to 37° C. Following incubation, the sample-contacted surface is washed to remove non-immunocomplexed material. The washing procedure may include washing with a solution such as PBS/Tween, or a borate buffer.

Following formation of specific immunocomplexes between the test sample and the bound FlaC protein, analogs, fragments and/or peptides, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a color development upon incubating with an appropriate chromogenic substrate. Quantification may then be achieved by measuring the degree of color generation using, for example, a visible spectra spectrophotometer.

3. Use of Sequences as Hybridization Probes

The nucleotide sequences of the present invention, comprising the sequence of the FlaC protein, fragments or analogs thereof, now allow for the identification and cloning of the FlaC protein genes from any species of Campylobacter and other bacteria that have FlaC protein genes.

The nucleotide sequences comprising the sequence of the basal body rod protein genes of the present invention are useful for their ability to selectively form duplex molecules with complementary stretches of other FlaC protein genes. Depending on the application, a variety of hybridization conditions may be employed to achieve varying degrees of selectivity of the probe toward the other FlaC protein genes. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. In general, convenient hybridization temperatures in the presence of 50% formamide are: 42° C. for a probe which is 95 to 100% homologous to the target fragment, 37° C. for 90 to 95% homology and 32° C. for 85 to 90% homology.

In a clinical diagnostic embodiment, the nucleic acid sequences of the basal body rod protein genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag such as urease, alkaline phosphatase or peroxidase, instead of a radioactive tag may be used. In the case of enzyme tags, calorimetric indicator substrates are known which can be employed to provide a means visible to the human eye or spectrophotometrically, to identify specific hybridization with samples containing TfR gene sequences.

The nucleic acid sequences of FlaC protein genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids or even tissues, is adsorbed or otherwise affixed to a selected matrix or surface. The fixed, single-stranded nucleic acid is then subjected to specific hybridization with selected probes comprising the nucleic acid sequences of the FlaC protein genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. As with the selection of peptides, it is preferred to select nucleic acid sequence portions which are conserved among species of bacteria (including Campylobacter) that produce FlaC proteins. The selected probe may be at least 18 bp and may be in the range of 30 bp to 90 bp long.

4. Expression of the FlaC Flagellin Protein Genes

Plasmid vectors containing replicon and control sequences which are derived from species compatible with the host cell may be used for the expression of the Flac protein genes in expression systems. The vector ordinarily carries a replication site, as well as marking sequences which are capable of providing phenotypic selection in transformed cells. For example, *E. coli* may be transformed using pBR322 which contains genes for ampicillin and tetracycline resistance and thus provides easy means for identifying transformed cells. The pBR322 plasmid, or other microbial plasmid or phage must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. Coli* LE392.

Promoters commonly used in recombinant DNA construction include the b-lactamase (penicillinase) and lactose promoter systems (Refs. 28, 29, 30) and other microbial promoters such as the T7 promoter system (U.S. Pat. No. 4,952,496). Details concerning the nucleotide sequences of promoters are known, enabling a skilled worker to ligate them functionally with genes. The particular promoter used will generally be a matter of choice depending upon the desired results. Hosts that are appropriate for expression of the basal body rod protein genes, fragments, analogs or variants thereof include *E. coli,* Bacillus species, Campylobacter, fungi, yeast or the baculovirus expression system may be used.

In accordance with this invention, it is preferred to make the protein by recombinant methods, particularly when the naturally occurring FlaC protein as purified from a culture of a species of Campylobacter may include trace amounts of toxic materials or other contaminants. This problem can be avoided by using recombinantly produced FlaC protein in heterologous systems which can be isolated from the host in a manner to minimize contaminants in the purified material. Particularly desirable hosts for expression in this regard include Gram positive bacteria which do not have LPS and are therefore endotoxin free. Such hosts include species of Bacillus and may be particularly useful for the production of non-pyrogenic basal body rod proteins, fragments or analogs thereof.

As noted above, bacteria that lack functional flagella and are substantially reduced in motility are also reduced in virulence. The nucleic acid molecules encoding FlaC proteins of flagella as provided herein allow for the specific modification of flagella (by, for example, site-specific mutagenesis of the genes encoding the basal body proteins) to functionally disable the flagella. Bacteria having such functionally disabled flagella will be rendered substantially non-motile and substantially avirulent. Such avirulent (or attenuated) bacteria are useful as immunogens for vaccination against disease caused by Campylobacter or other bacteria that produced flagella containing FlaC proteins as encoded by genes of the present invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, immunology and fermentation technology used but not explicitly described in this disclosure and these Examples are amply reported in the scientific literature and are well within the ability of those skilled in the art.

Example 1

This Example describes the analysis of a clone encoding the FlaC protein of the flagella of *Campylobacter jejuni*.

In ref. 4, are described the cloning and sequencing of the *C. jejuni* fur gene and four Fur-box sequences were identified in the 5' flanking region. Oligonucleotides corresponding to the Fur-box sequences were used as probes to screen a pBluescript genomic library of *C. jejuni* to attempt to isolate Fur-regulated genes.

One of the clones, plasmid pD2-2 (FIG. 2) contains the flaC gene of *C. jejuni*. The flaC gene in plasmid pD2-2 was sequenced by the dideoxy-chain termination method (reference 39 from paper) using the Sequenase kit from United States Biomedical or by the cycle sequencing kit from Pharmacia. When necessary, synthetic oligonucleotide primers were used in order to sequence of both strands. The determined nuclotide sequence (SEQ ID No: 1) is shown in FIG. 1.

A 16-mer oligonucleotide, 5' ATTGCGCGAACAGCTG 3', located on the complementary strand of the flaC gene at nt 314 to 298 was used to locate the transcriptional start point of this gene. Three transcriptional start points were detected at nt 183, nt 184, and nt 185. Using the flaC encoding fragment as a probe, a single hybridizing RNA band of 2.0 kb was seen in a Northern blot analysis.

The flaC gene (SEQ ID No: 1) is a 747 nt sequence encoding a protein of 249 amino acids (FIG. 1) (SEQ ID No: 3). The deduced molecular weight of this protein (FlaC) is 26.6 kDa. Nine nucleotides preceeding the Met start codon is a good matched Shine-Dalgarno sequence AGAAGG. At nt 167–174 is the –10 sequence (AATGATTA) and nt 145–148 is the –35 sequence (TTAA) of the typical sigma 28 promoter sequences (FIG. 1). The stop codon for the flaC gene is located at nucleotide 958.

Using pulsed field gel electrolysis and the flaC gene as a probe in a Southern blot, the gene was mapped to the SalI-D fragment (ref. 31). FlgFG genes have been mapped to the same fragment and the flaC gene is located less than 15 kb to the left (counterclockwise) from the basal rod genes (flgFG). The flaC gene is mapped on the opposite side of the genome from where the flaAB gene cluster is located and are separated by about 800 to 1000 kb.

Southern blot hybridization was performed in 30% formamide using a 0.5 kb PvuII fragment from the coding region of flaC (FIG. 3). The hybridization identified a single 0.8 kb HindIII band in all the *C. jejuni* strains tested, a 1.4 kb and a 1.1 kb band were detected in *C. coli* ATCC 33559 and ATCC 43474, respectively, a 1.8 kb band in *C. lari* ATCC 35221 and PC637 as well as a 0.5 kb band in *C. upsaliensis* ATCC 43954. These results suggest the pressure of a flaC homology among all the Campylobacter species and strains which were tested.

Using high stringency hybridization conditions (50% formamide), only the band in the *C. jejuni* and *C. coli* strains was detected. For *C. jejuni* OH4382, the 0.8 kb band was faint, owing to insufficient DNA. The presence of the band was confirmed by a subsequent hybridization with the flaC probe using a filter with equal amounts of genomic DNA from the three *C. jejuni* strains. The 0.8 kb band was detected with equal intensity in all three strains.

SUMMARY OF THE DISCLOSURE

In summary of this disclosure, the flaC gene of *Campylobacter jejuni* has been cloned and sequenced. The structural organization of the three flagellin genes in *C. jejuni* is clearly different as flaC is mapped on the opposite side of the genome from where the flaAB cluster islocated. Expression of the flaC gene can clearly be detected and a strong transcriptional start site can be demonstrated. Modifications are possible within the scope of this invention.

LIST OF REFERENCES

1. Penner J. L., (1988) Clin. Microbiol. Rev. 1: 157.
2. Macnab, Robert M. (1992) Annu. Rev. Genet. 26: 131.
3. Blaser, M. J. and L. B. Reller. (1981) New Engl. J. Med. 305: 1444–1452
4. Chan, V. L. et al., (1995) Gene 164:25–31.
5. Grant, C. C. R. et al., (1993) Infect. Immun. 61:1764–1771.
6. Guerry, P. et al., (1991) J. Bacteriol. 173:4757–4764.
7. Morooka, T. A. et al., (1985) J.Gen. Microbiol. 131:1973–1980.
8. Wassenaar, T. M. et al., (1995) Can. J. Microbiol. 141:95–101.
9. Tao, R. et al., (1994) Mol. Microbiol. 14:883–893.
10. Newell, D. G. et al., (1985) J. Hyg. 95:217–227.
11. Pavlovskis, O. R. et al., (1991) Infect. Immun. 59:2259–2264.
12. Macnab, R. M. (1996) In Neidhardt F. C. et al., (ed.) 123–145.
13. Alm, R. A. et al., (1993) J. Bacteriol. 175:3051–3057.
14. Driks, A. R. et al., (1989) J. Mol. Biol. 206:627–636.
15. Fisher, S. H. and I. Nachamkin. (1991) Mol. Microbiol. 5:1151–1158.
16. Josenhans C. A. et al., (1995) J. Bacteriol. 177:3010–3020.
17. Khawaja, R. K. et al., (1992) Curr. Microbiol. 24:213–221.
18. Kostrzynska, M. et al., (1991) J. Bacteriol. 173:937–946.
19. McCarter, L. L. (1995) J. Bacteriol. 177:1595–1609.
20. Minnich, S. A. et al., (1988) J. Bacteriol. 170:3953–3960.
21. Nuijten, P. J. M. et al., (1990) J. Biol. Chem. 265:17798–17804.
22. Pleier, E. and R. Schmitt. (1991) J. Bacteriol. 173:2077–2085.
23. O'Hagan (1992) Clin Pharmokinet. 22:1.
24. Ulmer et al., (1993) Curr. Opinion Invest. Drugs. 2(9): 983–989.
25. Nixon-George et al., (1990) J. Immunol. 14:4798.
26. Weismuller et al., (1989) Vaccine 8:29.
27. Deres et al., (1989) Nature 342:651.
28. Chang et al., (1978) Nature 375:615.
29. Itakura et al., (1977) Science 198:1056.
30. Goeddel et al., (1979) Nature 281:544.
31. Kim et al, J. Bacteriol. 175: 7468–7470

What we claim is:

1. A recombinant FlaC protein of a strain of Campylobacter producible by a transformed host cell containing an expression vector adapted for transformation of the host cell comprising a nucleic acid molecule which is selected from the group consisting of:

(a) the entire nucleotide sequence set out in FIG. 1 (SEQ ID No: 1), or the complementary sequence of said sequence;

(b) the coding nucleotide sequence set out in FIG. 1 (SEQ ID No: 2), or the complementary sequence of said sequence;

(c) a nucleotide sequence encoding the amino acid sequence set out in FIG. 1 (SEQ ID No: 3); and (d) a nucleotide sequence encoding a flagellin protein C (FlaC) of a flagellin of a strain of Campylobacter and which has at least about 90% sequence identity with any one of the nucleotide sequences defined in (a), (b) or (c), and expression means operatively coupled to the nucleic acid molecule for expression by the host cell of the FlaC protein of a strain of Campylobacter.

2. An isolated and purified FlaC protein of a Campylobacter strain, free from other proteins of the Campylobacter strain.

3. The FlaC protein of claim 2 wherein said strain of Campylobacter is a *Campylobacter jejuni* strain.

4. An immunogenic composition, comprising at least one active component selected from the group consisting of:

(A) a recombinant FlaC protein of a strain of Campylobacter producible in a transformed host cell containing an expression vector comprising a nucleic acid molecule which is selected form the group consisting of:

(a) the entire nucleotide sequence set out in FIG. 1 (SEQ ID No: 1), or the complementary sequence of said sequence;

(b) the coding nucleotide sequence set out in FIG. 1 (SEQ ID No: 2), or the complementary sequence of said sequence;

(c) a nucleotide sequence encoding the amino acid sequence set out in FIG. 1 (SEQ ID No: 3); and (d) a nucleotide sequence encoding a flagellin protein C (FlaC) of a flagellin of a strain of Campylobacter and which has at least about 90% sequence identity with any one of the nucleotide sequences defined in (a), (b) or (c), and expression means operatively coupled to the nucleic acid molecule for expression by the host cell of the FlaC protein of a strain of Campylobacter or (B) an isolated and purified FlaC protein of a Campylobacter strain free from other proteins of the Campylobacter strain;

and a pharmaceutically acceptable carrier therefor, said at least one active component producing an immune response when administered to a host.

* * * * *

SEQUENCE LISTING

<160> NUMBER OF SEQ ID NOS: 4

<210> SEQ ID NO 1
<211> LENGTH: 1105
<212> TYPE: DNA
<213> ORGANISM: Campylobacter jejuni

<400> SEQUENCE: 1

| | | | | | |
|---|---|---|---|---|---|
| atttgttttt | tattttacta | ataccataat | tgaactccaa | aacttaggcg | aaaacactac | 60 |
| aaaaactcaa | gaatttatca | gcatccataa | tgcaagtgaa | gtggtgatta | aaatcatctt | 120 |
| gataatgcaa | gttttttttat | atttcttaag | ctttaaaata | gcaaaaaaat | gataaaatat | 180 |
| taaataaatc | caaagagaaa | ggagtaggcc | atgatgatct | ctgatgcaac | tatgatgcaa | 240 |
| caaaattatt | atttaaataa | tgcacaaaaa | gctagcgata | aagctttaga | aaatattgca | 300 |
| gctgttcgcg | caataagtgg | agttgatagt | gctaatttag | ctattgctga | ttctttaaga | 360 |
| tctcaatcaa | gcactataga | tcaaggtgtc | gcaaatgctt | atgatgctat | agggttttta | 420 |
| caaattgcag | atgctagcct | taccaatatc | tctcaaagcg | cagatagact | taatgaactt | 480 |
| tcagtaaaaa | tgaacaatgc | tgcacttaat | gattctcaaa | aaggaatgct | aagaacagaa | 540 |
| gcaacacgca | tacaagaatc | catcaatgat | tcttttaata | atgcaactta | taatggaaaa | 600 |
| aatgtctttc | aaactatgaa | ttttgtagta | ggtagcggaa | ctgaaactac | aaatttaaat | 660 |
| ccattagcaa | cagatggatt | aagcatagat | aatcaagata | gtattacaaa | ttttatggat | 720 |
| caacttggaa | gtttaagaag | tgaaataggc | tcaggtatca | atgccatcac | atcaaatatt | 780 |
| aatgcaagtg | ttcaaaatag | catcaactca | aaagcagctg | aaaataattt | actaaataat | 840 |
| gacatggcaa | aaaatgtcaa | tgattttaat | gccaattatc | taaaagaaaa | tgctgctgct | 900 |
| tttgttgctg | cgcaatccaa | catgcagctt | caaagcaaaa | ttgctaattt | attacaataa | 960 |
| aataagccct | aaatagggct | tattttttat | caaaatgact | ttagagcaaa | ttttagaaaa | 1020 |
| aaccaaaaac | gttcgtcttg | tagcggcaag | caagtatgtc | gatgcaagta | taattgaaaa | 1080 |
| gcttttttgat | caaggtatag | tagaa | | | | 1105 |

<210> SEQ ID NO 2
<211> LENGTH: 747
<212> TYPE: DNA
<213> ORGANISM: Campylobacter jejuni

<400> SEQUENCE: 2

| | | | | | |
|---|---|---|---|---|---|
| atgatgatct | ctgatgcaac | tatgatgcaa | caaaattatt | atttaaataa | tgcacaaaaa | 60 |
| gctagcgata | aagctttaga | aaatattgca | gctgttcgcg | caataagtgg | agttgatagt | 120 |
| gctaatttag | ctattgctga | ttctttaaga | tctcaatcaa | gcactataga | tcaaggtgtc | 180 |
| gcaaatgctt | atgatgctat | agggttttta | caaattgcag | atgctagcct | taccaatatc | 240 |
| tctcaaagcg | cagatagact | taatgaactt | tcagtaaaaa | tgaacaatgc | tgcacttaat | 300 |
| gattctcaaa | aaggaatgct | aagaacagaa | gcaacacgca | tacaagaatc | catcaatgat | 360 |
| tcttttaata | atgcaactta | taatggaaaa | aatgtctttc | aaactatgaa | ttttgtagta | 420 |
| ggtagcggaa | ctgaaactac | aaatttaaat | ccattagcaa | cagatggatt | aagcatagat | 480 |
| aatcaagata | gtattacaaa | ttttatggat | caacttggaa | gtttaagaag | tgaaataggc | 540 |
| tcaggtatca | atgccatcac | atcaaatatt | aatgcaagtg | ttcaaaatag | catcaactca | 600 |
| aaagcagctg | aaaataattt | actaaataat | gacatggcaa | aaaatgtcaa | tgattttaat | 660 |

```
gccaattatc taaaagaaaa tgctgctgct tttgttgctg cgcaatccaa catgcagctt      720
caaagcaaaa ttgctaattt attacaa                                         747

<210> SEQ ID NO 3
<211> LENGTH: 249
<212> TYPE: PRT
<213> ORGANISM: Campylobacter jejuni

<400> SEQUENCE: 3

Met Met Ile Ser Asp Ala Thr Met Met Gln Gln Asn Tyr Tyr Leu Asn
 1               5                  10                  15

Asn Ala Gln Lys Ala Ser Asp Lys Ala Leu Glu Asn Ile Ala Ala Val
            20                  25                  30

Arg Ala Ile Ser Gly Val Asp Ser Ala Asn Leu Ala Ile Ala Asp Ser
        35                  40                  45

Leu Arg Ser Gln Ser Ser Thr Ile Asp Gln Gly Val Ala Asn Ala Tyr
    50                  55                  60

Asp Ala Ile Gly Val Leu Gln Ile Ala Asp Ala Ser Leu Thr Asn Ile
65                  70                  75                  80

Ser Gln Ser Ala Asp Arg Leu Asn Glu Leu Ser Val Lys Met Asn Asn
                85                  90                  95

Ala Ala Leu Asn Asp Ser Gln Lys Gly Met Leu Arg Thr Glu Ala Thr
            100                 105                 110

Arg Ile Gln Glu Ser Ile Asn Asp Ser Phe Asn Asn Ala Thr Tyr Asn
        115                 120                 125

Gly Lys Asn Val Phe Gln Thr Met Asn Phe Val Val Gly Ser Gly Thr
    130                 135                 140

Glu Thr Thr Asn Leu Asn Pro Leu Ala Thr Asp Gly Leu Ser Ile Asp
145                 150                 155                 160

Asn Gln Asp Ser Ile Thr Asn Phe Met Asp Gln Leu Gly Ser Leu Arg
                165                 170                 175

Ser Glu Ile Gly Ser Gly Ile Asn Ala Ile Thr Ser Asn Ile Asn Ala
            180                 185                 190

Ser Val Gln Asn Ser Ile Asn Ser Lys Ala Ala Glu Asn Asn Leu Leu
        195                 200                 205

Asn Asn Asp Met Ala Lys Asn Val Asn Asp Phe Asn Ala Asn Tyr Leu
    210                 215                 220

Lys Glu Asn Ala Ala Ala Phe Val Ala Ala Gln Ser Asn Met Gln Leu
225                 230                 235                 240

Gln Ser Lys Ile Ala Asn Leu Leu Gln
                245

<210> SEQ ID NO 4
<211> LENGTH: 16
<212> TYPE: DNA
<213> ORGANISM: Campylobacter jejuni

<400> SEQUENCE: 4
attgcgcgaa cagctg                                                      16
```